United States Patent
Kapre et al.

(10) Patent No.: US 10,702,596 B2
(45) Date of Patent: Jul. 7, 2020

(54) POLYSACCHARIDE PURIFICATION FOR VACCINE PRODUCTION USING LYTIC ENZYMES, TANGENTIAL FLOW FILTRATION, AND MULTIMODE CHROMATOGRAPHY

(71) Applicant: Inventprise, LLC, Redmond, WA (US)

(72) Inventors: Subhash V. Kapre, Redmond, WA (US); Anup K. Datta, Renton, WA (US)

(73) Assignee: Inventprise, LLC, Redmond, WA (US)

( * ) Notice: Subject to any disclaimer, the term of this patent is extended or adjusted under 35 U.S.C. 154(b) by 0 days.

(21) Appl. No.: 16/585,385

(22) Filed: Sep. 27, 2019

(65) Prior Publication Data

US 2020/0023050 A1    Jan. 23, 2020

Related U.S. Application Data

(63) Continuation-in-part of application No. 16/023,425, filed on Jun. 29, 2018, now Pat. No. 10,435,433.

(60) Provisional application No. 62/528,683, filed on Jul. 5, 2017.

(51) Int. Cl.
| | |
|---|---|
| C12P 19/04 | (2006.01) |
| A61K 39/09 | (2006.01) |
| A61K 39/095 | (2006.01) |
| A61K 39/112 | (2006.01) |
| A61K 39/102 | (2006.01) |

(52) U.S. Cl.
CPC ........ A61K 39/092 (2013.01); A61K 39/0275 (2013.01); A61K 39/095 (2013.01); A61K 39/102 (2013.01)

(58) Field of Classification Search
CPC .................................................. A61K 39/092
See application file for complete search history.

(56) References Cited

U.S. PATENT DOCUMENTS

| | | | | |
|---|---|---|---|---|
| 4,210,641 A | * | 7/1980 | Brossard | A61K 31/715 424/256.1 |
| 4,242,501 A | | 12/1980 | Cano | |
| 5,019,502 A | | 5/1991 | Rienstra | |
| 5,714,354 A | | 2/1998 | Arnold | |
| 5,847,112 A | | 12/1998 | Kniskern | |
| 5,952,454 A | * | 9/1999 | Kovac | A61K 39/385 525/54.1 |
| 7,550,145 B2 | * | 6/2009 | O'Hagan | A61K 39/39 424/184.1 |
| 8,946,395 B1 | | 2/2015 | Herigstad | |
| 2008/0286838 A1 | | 11/2008 | Yuan | |
| 2008/0292662 A1 | * | 11/2008 | Rhee | A61K 39/092 424/244.1 |
| 2010/0272755 A1 | | 10/2010 | Costantino | |
| 2012/0052088 A1 | * | 3/2012 | Davis | A61K 39/092 424/197.11 |
| 2013/0280274 A1 | | 10/2013 | Abbvie | |
| 2014/0011265 A1 | | 1/2014 | Kapre | |
| 2016/0067325 A1 | | 3/2016 | Damotharan et al. | |

FOREIGN PATENT DOCUMENTS

| | | |
|---|---|---|
| WO | WO 2006/082527 | 8/2006 |
| WO | WO 2008/045852 | 4/2008 |
| WO | WO 2012/127485 | 9/2012 |

OTHER PUBLICATIONS

International Search Report and Opinion for PCT/US2018/40296 dated Sep. 20, 2018.
"Lysis Buffer" Publication Date Nov. 8, 2016, retrieved date Sep. 5, 2018, https://en.wikipedia.org/w/index.php?title+Lysis_buffer&oldid+748422275, pp. 1-5.
Hessel "Experience with *Salmonella typhi* VI capsular polysaccharide vaccine" Eur. J. Clin. Microbial. Infect. Dis., vol. 18(9), pp. 609-620, Sep. 1999.
"Purification of Capsular Polysaccharide Produced by *Streptococcus pneumoniae* Serotype 19A" *J. Microbiol. Biotechnol*, 21(7), 734-738, 2011.
"Production of Capsular Polysaccharide of *Streptococcus pneumoniae* Type 14 and Its Purification by Affinity Chromatography," *Appl Environ Microbiol*, 67(2): 969-971, Feb. 2011.

\* cited by examiner

*Primary Examiner* — Albert M Navarro
(74) *Attorney, Agent, or Firm* — Remenick PLLC

(57) ABSTRACT

An improved, cost effective and shortened process of purification of the capsular polysaccharide of *S. pneumoniae*, Group B *Streptococcus, H. influenzae, S. typhoid* and *N. meningitidis* is disclosed. The process includes a cocktail of enzyme treatment, tangential flow filtration, and multimodal chromatography purification. For Gram-negative bacteria, endotoxin removal process involves endotrap HD resin. This shortened process achieved the purity required by WHO/EP/BP for the use in human vaccine preparation, with simple steps and higher yield as compared to conventional processes. The steps of the process avoid use of organic solvents such as, for example, alcohol, phenol, and ultracentrifugation that are otherwise expensive and time consuming to perform, and/or health hazards for commercial use. This process disclosed is also simple, efficient, non-toxic, easy to scale-up, and environmentally friendly.

34 Claims, 2 Drawing Sheets

POLYSACCHARIDE PURIFICATION FOR VACCINE PRODUCTION USING LYTIC ENZYMES, TANGENTIAL FLOW FILTRATION, AND MULTIMODE CHROMATOGRAPHY

REFERENCE TO RELATED APPLICATIONS

This application is a continuation-in-part of U.S. application Ser. No. 16/023,425 filed Jun. 29, 2018, which issued as U.S. Pat. No. 10,435,433 on Oct. 8, 2019, which claims priority to U.S. Provisional Application No. 62/528,683 filed Jul. 5, 2017, the entirety of each of which is hereby incorporated by reference.

BACKGROUND

1. Field of the Invention

The present invention is directed to processes and compositions for the effective purification of bacterial polysaccharide. Processes are efficient, cost effective, and scalable and involve removing impurities for the preparation of vaccines including conjugate vaccines.

2. Description of the Background

Purified CPS (capsular polysaccharides) are used in the production of vaccines and especially vaccines that are effective against infection produced by the bacteria from which the CPS were derived. In a conventional process, bacteria are cultivated in industrial bioreactors and CPS purified to predetermined or desired purity requirements. A traditional purification process of bacterial CPS for vaccine production is based on several selective precipitations steps with solvents like ethanol and phenol, and cationic detergents.

*H. influenzae, N. meningitidis,* Group B *Streptococcus,* and *S. pneumonia* are some of the most common agents of meningitis, pneumonia and bacteremia in infants and immunodeficient adults. The capsular polysaccharides (CPS) act as mechanisms of defense against the immune system of the hosts which makes them the main factor of virulence of these bacteria. Vaccines based on polysaccharides derived from these organisms are effective for the adult population. There are several studies about the immunogenic characteristics of polysaccharide vaccines. The purification process aims to obtain the product with the desired specification while maximizing yield and minimizing process cost. The final purification step of the conventional procedure involves a series of purification steps where there is a trade-off between production efficiency and removal of contaminants. The contaminants in the purification of CPS are, for example, proteins, nucleic acids, pigments and undesired polysaccharides, e.g. cell wall polysaccharides for Gram-positive bacteria or lipopolysaccharides (LPS) for Gram-Negative bacteria.

Conventional purification processes of CPS follow a general method of concentration/purification by ethanol and/or anionic detergent selective precipitation, protein extraction by phenol and, for Gram-negative bacteria, by ultracentrifugation to eliminate the LPS.

For example, conventional purification of polysaccharides from *N. meningitidis* includes precipitation with cationic detergent cetavlon, precipitate is resuspended in 1 M $CaCl_2$), two precipitations with ethanol, deproteinization by three extraction steps with phenol, dialysis and further ethanol precipitation. LPS is separated from the CPS by ultracentrifugation.

The conventional purification process for *S. pneumoniae* CPS includes total cell lyses with detergent deoxycholate, concentration/diafiltration, four steps of ethanol precipitation, deproteinization by phenol treatment and activated charcoal.

The conventional purification process for *H. influenzae* PRP starts with the inactivation of the cells by phenol, formaldehyde or thimerosal and the separation of the culture broth by centrifugation. The clarified supernatant is then concentrated by tangential flow ultrafiltration with a 50-100 kDa cut-off membrane, precipitated with cationic detergent cetavlon and the complex PRP-cetavlon solubilized with calcium chloride followed by several ethanol precipitations and deproteinization by extraction with phenol and further ethanol precipitation. The lipopolysaccharides are separated from the PRP by ultracentrifugation.

A number of purification procedures are currently available that are directed to the removal of protein and other impurities such as cell-wall C-polysaccharide from capsular polysaccharides. For example, U.S. Pat. No. 4,242,501 is directed to purification of pneumoccal capsular polysaccharide and relates to a method for the removal of protein and other impurities (C-polysaccharide) from microbial capsular polysaccharides. 1572 MUM/2010. U.S. Pat. Nos. 5,714,354, 5,847,112, and 4,242,501 are each directed to purification processes from pneumococcal polysaccharide. International Publication No. WO 2006/082527 relates to a purification process for the capsular polysaccharide of *S. agalactiae* which involves precipitation with a cationic detergent. International Application Publication No. WO 2008/045852 relates to a process for the purification of pneumococcal polysaccharide wherein heating and low pH precipitation process were employed. International Application Publication No. WO 2012/127485 relates to an alcohol and CTAB free method for the purification of pneumococcal polysaccharides. Other publications regarding CPS purifications include "Purification of Capsular Polysaccharide Produced by *Streptococcus pneumoniae* Serotype 19A" *J. Microbiol. Biotechnol,* 21(7), 734-738, 2011; "Production of Capsular Polysaccharide of *Streptococcus pneumoniae* Type 14 and Its Purification by Affinity Chromatography," *Appl Environ Microbiol,* 67(2): 969-971, February 2011.

Conventional CPS purification processes are long and involved, and require highly trained individuals and utilize a number of costly supplies and compositions. In addition, the risk of errors is great and error often occur making the process highly inefficient in both time and resources. Thus, there remains a need for efficient and effective polysaccharide purification procedures.

SUMMARY OF THE INVENTION

The present invention overcomes the problems and disadvantages associated with current strategies and designs, and provides new compositions and procedures for purifying polysaccharides.

One embodiment of the invention is directed to processes of purifying bacterial cell surface polysaccharides comprising: providing a fermentation harvest of Gram-positive and/or Gram-negative bacteria. The fermentation harvest is clarified, preferably with deoxycholate or a functionally similar at an acidic pH, such as pH 3.5-5.0. The clarified polysaccharide is preferably concentrated by diafiltration and treated with an enzyme for removal of impurities such as host cell proteins, nucleic acids, and cell wall polysaccharide which may be attached to peptidoglycan and/or other cell membrane structures. The enzyme is precipitated preferably with acetic acid and the enzyme treated polysaccharide is concentrated by diafiltration and passed through multimodal chromatographic resin in flow-through mode, tangential flow filtration, and/or filtration through CAPTO™ Adhere resin. Preferably the bacterial cell surface polysaccharide comprises a capsular polysaccharide and/or an exopolysaccharide. Preferably the harvest of bacteria comprises S. pneumoniae, Group B Streptococcus, H. influenzae, S. typhimurium or N. meningitis. Preferably, clarifying is followed by pH adjustment at acidic pH 3.5-5 using acetic acid or below pH 3.5 or below pH 4.5 using 2M acetic acid. Preferably the enzyme is selected from the group consisting of Benzonase, Mutanolysin/lysozyme, β-D-N-acetyl glucosaminidase and Proteinase K. Preferably enzyme treatment is sequentially either singularly or in combination. Preferably the fermentation harvest comprises Gram-negative bacterial and the enzyme treated and diafiltered polysaccharide is passed through tangential flow filtration using a deoxycholate/EDTA/Ca-salt buffer. Preferably the tangential flow filtration includes passage of the polysaccharide through a 50-100 kDa membrane. Preferably the fermentation harvest comprises Gram-positive bacterial and the enzyme treated and diafiltered polysaccharide is passed through multimodal chromatography with CAPTO™ Adhere resin. Preferably the fermentation harvest comprises Gram-negative bacterial and further comprising removal of endotoxin using resin chromatography more specifically EndoTrap HD resin in a flow through mode. Preferably the fermentation harvest comprises S. pneumoniae comprising one or more serotypes 1, 2, 3, 4, 5, 6A, 6B, 6C, 7F, 8, 9V, 9N, 10A, 11A, 12F, 14, 15A, 15B, 15C, 17F, 18C, 19A, 19F, 20, 22F, 23F, 24, 24F, 33F and 35B or another serotypes used in vaccine preparation. Preferably the fermentation harvest comprises Group B Streptococcus comprising one or more of serotypes Ia, Ib, II, III, IV, V, VI, VII, VIII and IX. Preferably the fermentation harvest comprises H. influenzae comprising sub-strains a, b, c, d, e and f serotypes. Preferably the fermentation harvest comprises S. typhi comprising Vi-polysaccharide. Preferably the fermentation harvest comprises N. meningitis comprising of one or more serotypes A, B, C, X, Y, and W-135.

Another embodiment of the invention comprises a polysaccharide purified by the method of the invention as described herein.

Another embodiment of the invention comprises an immunological composition such as a vaccine that incorporates or is derived from the purified polysaccharide of the invention. Vaccines prepared according to this disclosure may or may not comprise adjuvants.

Other embodiments and advantages of the invention are set forth in part in the description, which follows, and in part, may be obvious from this description, or may be learned from the practice of the invention.

DESCRIPTION OF THE INVENTION

Figure 1:
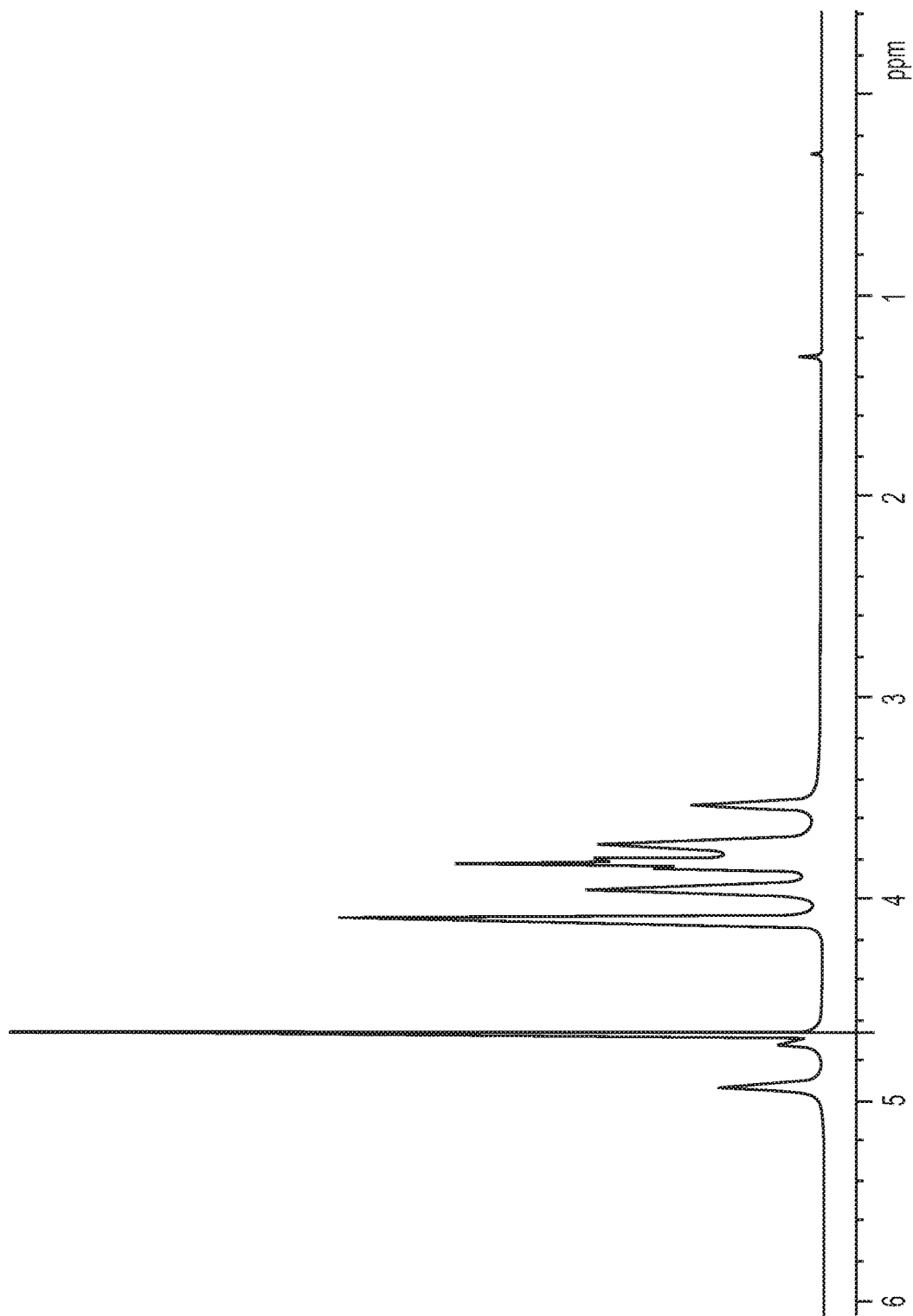
FIG. 1 $^1$H NMR analysis of purified polysaccharides which shows polysaccharide are free of cell wall polysaccharide (CWPS) using the purification strategy-1. S. pneumoniae type 3 polysaccharide, size reduced polysaccharide, molecular size distribution by SEC-HPLC-<50 kDa (C-polysaccharide undetected at 3.2 PPM).

Separations of solid from liquid are based on continuous centrifugation in purified CPS are used in the production of vaccines against these bacteria. Separations of solid from liquid are based on continuous centrifugation in explosion proof installations.

A method for CPS purification has been surprisingly developed that eliminates the ethanol precipitations, use of phenol, and the ultracentrifugation steps of conventional procedures. The process of this disclosure includes an ultrafiltration step using membranes with desired molecular weight cut-off values, such as for example 30-100 kDa, and eliminates residual proteins and nucleic acids by enzymatic digestion and tangential flow-filtrations (TFF) with, preferably, 30-100 kDa cut-off membranes. The resulting purified CPS has a yield of greater than 70% with less than or equal to 1% of protein and less than or equal to 1% of nucleic acid related to total CPS. The purified CPS are free of proteolytic enzymatic activity and passes necessary quality tests.

The general advantages of the present invention include providing a rapid, efficient and effective process for the purification of bacterial cell surface capsular polysaccharide (CPS) that purifies polysaccharides while eliminating the impurities in a very short time by simple, efficient, and commercially scalable steps thereby producing high quality polysaccharide that meets or exceeds the relevant WHO specifications and other quality standards.

One embodiment of the invention is directed to the process of purification of polysaccharide. The process describes a novel, rapid, cost effective, and scalable method, wherein polysaccharide is purified with significantly reduced time. The selected bacterial strain is cultivated on optimized cultivation media in the fermenter and the process proceeds by doing the centrifugation of the fermented harvest to remove cell debris followed by TFF using molecular weight cut-off membranes. The process of the invention exhibits several advantages over prior art, such as providing a novel and rapid method of preparing polysaccharide. The process is cost effective as it reduces the total number of steps and requires single chromatographic screening. An additional advantage is that this process is entirely scalable Although the purification of most any polysaccharide can be performed in accordance with the methods this disclosure, in particular, preferred methods involve purification of polysaccharides from N. meningitidis, S. pneumoniae, H. influenzae type b, S. typhimurium, and Group B Streptococcus, for vaccine production. The method comprises providing a fermentation harvest of bacteria or other polysaccharide source, clarification of the fermentation harvest with deoxycholate at, for example, a pH of about 3.5 to about 7.0, preferably from about pH 4 to about pH 6.8 or from about pH 4.5 to about pH 6.5, concentration of the clarified polysaccharide by a first diafiltration and treatment of the first diafiltered polysaccharide with an enzyme to remove impurities, precipitation of the enzyme with acetic acid such that polysaccharide remains in a supernatant, concentration of the polysaccharide of the supernatant by a second diafiltration, passage of the second diafiltered polysaccharide through multimodal chromatographic resin and/or endotoxin removal resin. Preferably the chromatography is tangential flow filtration with deoxycholate/EDTA/Ca-salt buffer, or ion-exchange followed by hydrophobic interaction chromatography, and followed by collection of the purified polysaccharide.

Methods of this disclosure eliminate the need and use of ethanol, phenol, and detergent precipitations, and instead involve successive lytic enzymatic treatment followed by ultrafiltration and, if desired, preferably further purification by hydrophobic interaction chromatography or mixed mode ion exchange resin chromatography.

The nuclease, benzonase, hydrolyzes the residual genomic DNA and RNA and the resulting low molecular mass oligonucleotides are filtered through the membrane in the second TFUF. Peptidoglycan and cell wall polysaccharide (CWPS or Group B Carbohydrate) attach to peptidoglycan are degraded and/or size reduced by Mutanolysin/Lysozyme/β-D-N-acetyl glucosaminidase enzymatic (active unit ratio: 1:1:0.1) cocktail combination. Protein and LPS are eliminated after enzymatic treatment and a second concentration/diafiltration with TFUF 30-100 kDa. The elimination of LPS, for the Gram-negative bacteria, is preferably performed with TFUF in the presence of detergent and a chelating agent, preferably DOC/EDTA. The detergent deoxycholate, DOC, breaks the hydrophobic interaction of the fatty acids of the lipid part, disestablish the aggregate and produces low molecular mass monomers of LPS that can be freely filtrated in the membrane of 30-100 kDa.

The purification processes of the invention are, in part, based on molecular size. In the first TFUF, molecules with size less than the pore cut off are eliminated, most of them from the culture medium. After the enzymes reduce the size of the contaminants, proteins and nucleic acids, and the second TFUF provides for their elimination. Low molecular mass monomers from LPS are ultrafiltrated in the presence of detergent and chelating agent.

The processes of the invention eliminate a number of precipitations steps required in conventional processes that use alcohols, phenols, or cationic detergents, and instead involves enzymatic treatment and/or ultrafiltration to achieve final products at the required or desired purity.

Compared to ultracentrifugation, the combination of enzymatic treatment and tangential ultrafiltration is easier to scale-up and much cheaper. The membranes for tangential flow are cleaned in place and stored for repeated use (for example using disposable membranes). The method of the disclose provide a simple, efficient and environmentally friendly method that is easily scaled-up for commercial development.

Preferably the fermentation harvest comprises *S. pneumoniae* comprising one or more serotypes 1, 2, 3, 4, 5, 6A, 6B, 6C, 7F, 8, 9V, 9N, 10A, 11A, 12F, 14, 15A, 15B, 15C, 17F, 18C, 19A, 19F, 20, 22F, 23F, 24, 24F, 33F and 35B or another serotypes used in vaccine preparation. Preferably the fermentation harvest comprises Group B *Streptococcus* comprising one or more of serotypes Ia, Ib, II, III, IV, V, VI, VII, VIII and IX. Preferably the fermentation harvest comprises *H. influenzae* comprising sub-strains a, b, c, d, e and f serotypes. Preferably the fermentation harvest comprises *S. typhi* comprising Vi-polysaccharide. Preferably the fermentation harvest comprises *N. meningitis* comprising of one or more serotypes A, B, C, X, Y, and W-135.

The following examples illustrate embodiments of the invention, but should not be viewed as limiting the scope of the invention.

EXAMPLES

Example 1

Cultivation of Bacteria

Cultures of bacteria were conducted in a 5-10-L fermenter containing medium and conditions appropriate for each strain. The whole broth of the bioreactor, was precipitated with 0.15% deoxycholate, decanted and centrifuged. Cells were separated from the culture broth by tangential microfiltration. Cell-free micro filtrate was used for CPS-purification for *S. pneumoniae* and additional strains as well.
Concentration/Defiltration The cell-free CPS was concentrated to 1-20 fold by tangential flow ultrafiltration (TFUF) membranes of 30-100 kDa. The concentrate was biofiltered with buffer.
Enzymatic Treatment and Concentration/Diafiltration The pH of soluble-CPS fractions from *Neisseria* or *Streptococcus* were adjusted to pH 7. Recombinant enzymes were added successively: Benzonase (Tris-HCl 50 mM containing 2 mM $MgCl_2$ and 20 mM NaCl); Mmutanolysin/Lysozyme (1:1); β-D-N-acetyl glucosaminidase; and Proteinase K were added with a 2-4 hrs interval between them and incubated for 12-24 hours at 37° C.-56° C. under alkaline pH (pH 8.8-10.5) at 50-100 rpm. Low-molecular-mass contaminants resulting from enzymatic degradation and detergent treatment were eliminated by the second TFUF membrane of 30-100 kDa cut-off. Purified CPS was sterile filtered by a 0.2 μm membrane and stored at minus 20° C.

Two different purification strategies were used for purification of polysaccharides. One purification process was used generally for Gram-positive bacterial polysaccharide purification process (Purification Strategy-1) and one used for Gram-Negative bacterial polysaccharide purification process (Purification strategy-2).
Purification Strategy-1 (for Gram-Positive Bacteria)

Polysaccharide Purification Using Enzyme cocktail containing Benzonase, Mutanolysin/Lysozyme combination, β-D-N-acetyl-glucosaminidase, Proteinase K followed by tangential flow filtration (TFF) and finally multimodal anion-exchanger CAPTO™ Adhere Resin Chromatography (a multimodal medium resin designed for post-protein A purification of monoclonal antibodies at process scale).

Multiple serotypes polysaccharides either from *S. pneumoniae* and Group B Streptococcal serotypes were purified. All polysaccharides purified met or exceeded the criterion of WHO/or BP/or EP criterion for polysaccharide purity. Further purity was achieved by wt. to residual protein, nucleic acid and endotoxin multimodal chromatography steps. Multimodal chromatography was also used to remove the residual enzymes which were used during purification steps.
Cell Separation, Concentration by Tangential Ultrafiltration.

After cultivation of bacteria, fermented liquid was inactivated by 0.15% deoxycholate (pH was adjusted to 4.5-5), cells were removed by decanting followed by centrifugation, and cell-free clarified broth was concentrated and diafiltered using 50 KDa-100 KDa PES membrane using 0.9% saline followed by Tris-HCl buffer (50 mM, pH 7.0).
Enzymatic Treatment and Second Concentration by Tangential Ultrafiltration.

The polysaccharide solution pH was raised from pH 7.0 to pH 9-9.5, 2 mM $MgCl_2$ was added and incubated at 42° C. for 15 minutes at 50-75 rpm. The enzyme Benzonase was added, 10-20 unit per ml of PS solution and incubated for 1-2 hr. Subsequently the enzyme combination Mutanolysin/Lysozyme (1:1) at 50 unit per ml of solution was added and incubated for 1-2 hr. The enzyme β-N-acetyl-D-glucosaminidase was added at 1 unit/100 ml of polysaccharide solution. Proteinase K was added and incubated at 56° C. and pH 9.5-10.5 for 2-4 hr. Total enzymatic reaction was completed within 6-8 hrs. All enzymes used were recombinant enzymes.

After the enzymatic treatment, acetic acid (2M) was used to reduce the pH of the solution to 3.5-4.5, precipitates were removed by depth filtration and pH of the polysaccharide solution was adjusted to pH 7.0. Clarified polysaccharide solution was concentrated and diafiltered by 50 kDa-100 kDa PES membrane using 0.9% saline, followed by 50 mM sodium phosphate buffer (50 mM, pH 7.4-7.6).

Column Chromatography Using CAPTO™ Adhere Resin

Final purification of polysaccharide was achieved in simple flow-through mode using CAPTO™ Adhere resin chromatography and finally eluted by using 50 mM sodium phosphate+1.0M NaCl at pH 7.4-7.6. Results are shown in Table 1 and FIG. 1.

TABLE 1

Purification of *Streptococcus pneumoniae* and Group B *Streptococcus* polysaccharide serotypes

| PS serotype | % PS Recovery | % Protein | WHO TRS % Protein | % NA | WHO TRS % NA | SEC-HPLC kDa | Cell wall polysaccharide (CWPS) or Group B carbohydrate by $^1$H NMR |
|---|---|---|---|---|---|---|---|
| 3 | 78 | 0.85 | 7.5% | 0.10 | 2 | >800 | <1% |
| 19F | 65 | 0.28 | 3% | 0.04 | 2 | >300 | <1% |
| 1 | 68 | 0.65 | 2 | 0.03 | 2 | >300 | <1.5% |
| Ia | 65 | 0.75 | 3% | 0.18 | 2 | >300 | Below detection limit |
| III | 70 | 0.65 | 3% | 0.33 | 2 | >300 | 0.5% |
| V | 70 | 0.60 | 3% | 0.35 | 2 | >400 | Below detection limit |

Note:
% PS recovery was calculated from initial crude PS in fermenter

Purification Strategy-2 (for Gram-Negative Bacteria)

Polysaccharide purification using Enzyme cocktail containing benzonase, Proteinase K followed by tangential flow filtration (TFF), and multimodal anion-exchanger CAPTO™ Adhere Resin Chromatography and/or LPS removal by ENDOTRAP®-HD resin.

Multiple serotypes polysaccharides either from *H. influenzae, N. meningitis, S. typhimurium* serotypes were purified. All polysaccharides purified met or exceeded the criterion of WHO/or BP/or EP criterion for polysaccharide purity. Endotoxin removal steps were used to remove residual endotoxins. Multimodal chromatography was kept optional to remove the residual enzymes which were used during purification steps.

Cell Separation, Concentration by Tangential Ultrafiltration.

After cultivation of bacteria, the fermented liquid was inactivated by 0.15% deoxycholate or by 0.6% formaldehyde. Cells were removed by either decanting and/or centrifugation, and cell-free clarified broth was concentrated and diafiltered using 50 kDa-100 kDa PES membrane using 0.9% saline, followed by Tris-HCl buffer (50 mM, pH 7.0).

Enzymatic Treatment and Second Concentration by Tangential Ultrafiltration.

The pH of the polysaccharide solution was raised from 7.0 to 8.5-8.8, 2 mM $MgCl_2$ was added and incubated at 37° C. for 15 minutes at 50-75 rpm. The enzyme benzonase was added at 10-20 unit per ml of PS solution and the solution was incubated for 1-2 hr. Proteinase K was added and incubated at 45° C. at pH 9.5-10.5 for 2-4 hr. Total enzymatic reaction was completed within 6-8 hrs. All enzymes used were recombinant enzymes.

After enzymatic treatment, acetic acid (2M) was used to reduce the pH of the solution to 3.5-4.5. Precipitates were removed by depth filtration and pH of the polysaccharide solution was adjusted to pH 7.0. Clarified polysaccharide solution was concentrated and diafiltered by 50 kDa-100 kDa PES membrane using 0.2% DOC and 1-2 mM EDTA, followed by 50 mM Na-phosphate buffer (50 mM, pH 6.0-6.4) to reduce Endotoxin impurity.

Endotoxin Removal Using Endotrap HD Resin

Residual endotoxin in the polysaccharide solution was removed by using ENDOTRAP®-HD resin (endotoxin removal resin; Hyglos GmbH, Germany) in a simple flow-through mode. Buffers used are either 100-200 mM TRIS or HEPES at pH 6.4-7.4 with 50-80 mM NaCl. Calcium ions and EDTA present in the buffer also enhanced removal of endotoxin. ENDOTRAP®-HD resin can be used several times after regeneration.

Column Chromatography Using CAPTO™ Adhere Resin

Figure 2:
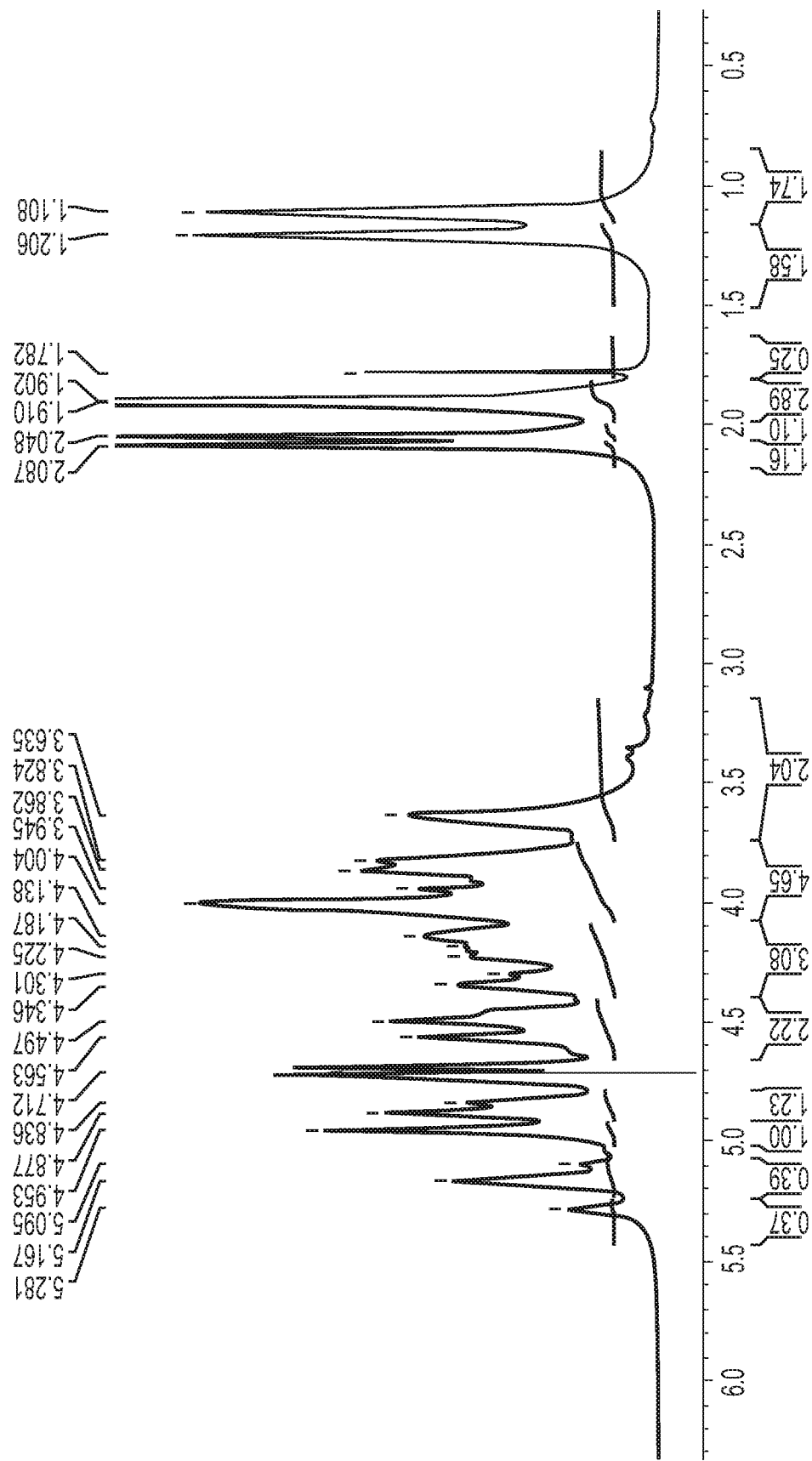
FIG. 2 $^1$H NMR analysis of purified polysaccharides which shows polysaccharide are free of cell wall polysaccharide (CWPS) using the purification strategy-1. S. pneumoniae type 1 polysaccharide—size reduced polysaccharide, molecular size distribution by SEC-HPLC-<50 kDa (C-polysaccharide undetected at 3.2 PPM).

Purification of polysaccharide was achieved in simple flow-through mode using CAPTO™ Adhere resin chromatography and eluted by using 50 mM sodium phosphate+1.0M NaCl at pH 7.4-7.6. This chromatography steps were kept optional if residual enzymes activity was observed and also if any leakage from ENDOTRAP®-HD resin was observed. Results are shown in Table 2 and FIG. 2.

TABLE 2

Purification of *H. influenzae* type a/b, *N. meningitis* type W-135, and *S. typhi* polysaccharide

| PS serotype | % Recovery (WHO TRS) | % Protein (WHO TRS) | % NA (WHO TRS) | SEC-HPLC Kd | Endotoxin EU/pg of PS (WHO TRS) |
|---|---|---|---|---|---|
| *H. Influenzae* type b | 70 | <0.3 (<1%) | <0.05 (<1%) | >400 | 1 Eu/μg of PS (10 Eu/μg) |
| *H. Influenzae* type a | 75 | <0.1 (<1%) | <0.03 (<1%) | >600 | 1 Eu/μg of PS (10 Eu/μg) |
| *S. typhi* | 65 | <1.0 (<3%) | <0.5 (<2%) | >600 | 5 Eu/μg of PS (10 Eu/μg) |
| *N. meningitis* W-135 | 75 | <1.0 (<3%) | <0.5 (<1%) | >400 | 5 Eu/μg of PS (10 Eu/μg) |

Other embodiments and uses of the invention will be apparent to those skilled in the art from consideration of the specification and practice of the invention disclosed herein. All references cited herein, including all publications, U.S. and foreign patents and patent applications, are specifically and entirely incorporated by reference. It is intended that the specification and examples be considered exemplary only with the true scope and spirit of the invention indicated by the following claims. Furthermore, the term "comprising of" includes the terms "consisting of" and "consisting essentially of."

The invention claimed is:

1. A polysaccharide composition obtained or derived from Gram-positive or Gram-negative bacteria, which has been treated with deoxycholate at a pH of about 3.5 to about 7.0, and an antimicrobial enzyme, wherein after being treated the composition contains 0.35 percent or less of nucleic acid and 0.85 percent or less of protein.

2. The composition of claim 1, wherein the antimicrobial enzyme comprises Benzonase, Mutanolysin/lysozyme, β-D-N-acetyl glucosaminidase and/or Proteinase K.

3. The composition of claim 2, wherein the antimicrobial enzyme comprises sequential treatment of the polysaccharide with Benzonase followed by Mutanolysin/Lysozyme (1:1), followed by β-N-acetyl-D-glucosaminidase, followed by Proteinase K.

4. The composition of claim 1, which has been precipitated with an acid, and purified by passage through multimodal chromatography.

5. The polysaccharide of claim 1, which has been passed through an endotoxin removal resin.

6. The composition of claim 4, wherein the multimodal chromatography comprises tangential flow filtration or ion-exchange followed by hydrophobic interaction chromatography.

7. The composition of claim 6, wherein the tangential flow filtration comprises deoxycholate/EDTA/Ca-salt buffer and/or passage through a 50-100 kDa membrane.

8. The composition of claim 1, wherein the bacteria comprise Gram-negative bacteria.

9. The composition of claim 1, wherein the bacteria comprise S. pneumoniae, Group B Streptococcus, H. influenzae, S. typhimurium and/or N. meningitis.

10. The composition of claim 1, wherein the bacteria comprise S. pneumoniae.

11. The composition of claim 10, wherein the S. pneumoniae comprising one or more of serotypes 1, 2, 3, 4, 5, 6A, 6B, 6C, 7F, 8, 9V, 9N, 10A, 11A, 12F, 14, 15A, 15B, 15C, 17F, 18C, 19A, 19F, 20, 22F, 23F, 24, 24F, 33F and 35B.

12. The composition of claim 1, wherein the bacteria comprises Group B Streptococcus.

13. The composition of claim 12, wherein the Group B Streptococcus comprising one or more of serotypes Ia, Ib, II, III, IV, V, VI, VII, VIII and IX.

14. The composition of claim 1, wherein the bacteria comprise H. influenza.

15. The composition of claim 14, wherein the H. influenza comprises one or more of serotypes a, b, c, d, e and f.

16. The composition of claim 1, wherein the bacteria comprise S. typhi.

17. The composition of claim 16, wherein the S. typhi comprising Vi-polysaccharide.

18. The composition of claim 1, wherein the bacteria comprise N. meningitis.

19. The composition of claim 18, wherein the N. meningitis comprises one or more serotypes A, B, C, X, Y, and W-135.

20. The composition of claim 1, which comprises a bacterial cell surface polysaccharide.

21. The composition of claim 20, wherein the bacterial cell surface polysaccharide comprises capsular polysaccharide and/or exopolysaccharide.

22. An immunological composition that contains the polysaccharide of claim 1.

23. The immunological composition of claim 22, further comprising an adjuvant.

24. The immunological composition of claim 22, that does not comprise an adjuvant.

25. An immunological composition that contains the composition of claim 10.

26. An immunological composition that contains the composition of claim 12.

27. An immunological composition that contains the composition of claim 14.

28. An immunological composition that contains the composition of claim 16.

29. An immunological composition that contains the composition of claim 18.

30. A polysaccharide composition obtained or derived from Gram-positive or Gram-negative bacteria, which has been treated with deoxycholate at a pH of about 3.5 to about 6.5, and an antimicrobial enzyme, wherein the antimicrobial enzyme comprises a sequential treatment of Benzonase, Mutanolysin/lysozyme, β-D-N-acetyl glucosaminidase and Proteinase K, and after being treated the composition contains 0.35 percent or less of nucleic acid and 0.85 percent or less of protein.

31. The composition of claim 1, which has an endotoxin level of about 5 EU or less per μg of polysaccharide.

32. The composition of claim 1, which has an endotoxin level of about 1 EU per μg of polysaccharide.

33. The composition of claim 30, which has an endotoxin level of about 5 EU or less per μg of polysaccharide.

34. The composition of claim 30, which has an endotoxin level of about 1 EU per μg of polysaccharide.

* * * * *